US00PP30509P2

(12) United States Plant Patent
Kordes

(10) Patent No.: US PP30,509 P2
(45) Date of Patent: May 21, 2019

(54) SHRUB ROSE PLANT NAMED 'KORCRACFIR'

(50) Latin Name: *Rosa hybrida*
Varietal Denomination: KORcracfir

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORGES' SÖHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,547

(22) Filed: Nov. 27, 2017

(51) Int. Cl.
*A01H 5/02* (2018.01)

(52) U.S. Cl.
USPC ..... Plt./106

(58) Field of Classification Search
USPC ..... Plt./106
See application file for complete search history.

(56) References Cited

U.S. PATENT DOCUMENTS

PP19,803 P2 * 3/2009 Radler ..... Plt./106

* cited by examiner

*Primary Examiner* — Annette H Para
(74) *Attorney, Agent, or Firm* — Buchanan Ingersoll & Rooney PC

(57) ABSTRACT

A new and distinct variety of Shrub Rose Plant, herein referred to by its cultivar name, 'KORcracfir', is provided which forms in abundance on a substantially continuous basis attractive, salmon-orange colored blossoms. The vegetation is vigorous and the growth habit is compact and bushy. Attractive semi-glossy, dark green foliage is formed. The resistance to disease is very good. The new variety is particularly well suited for providing distinctive ornamentation in the landscape.

3 Drawing Sheets

Figure 1:
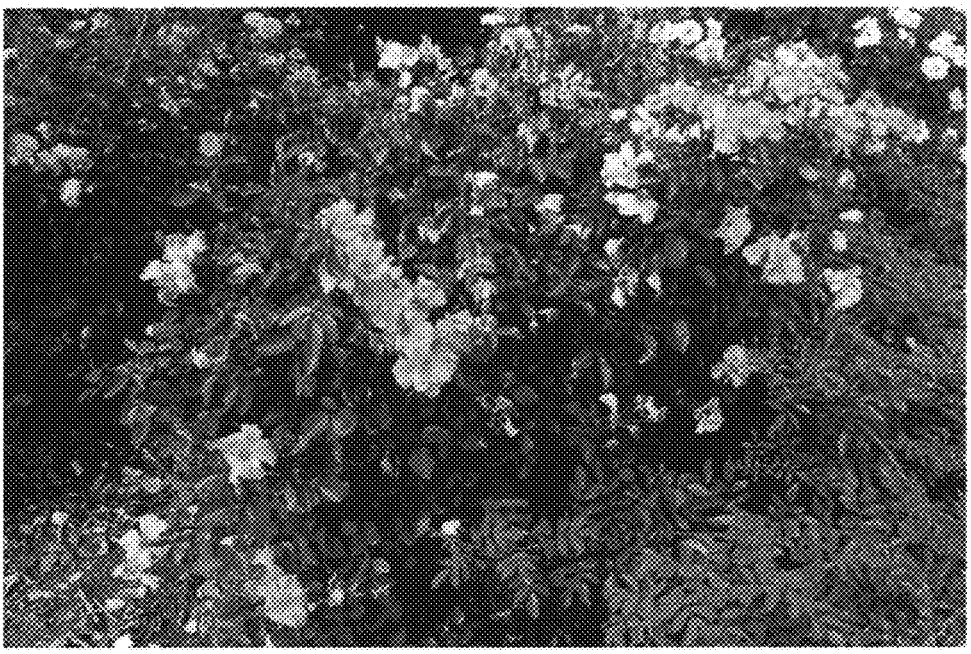

Botanical/commercial classification:
Latin name—*Rosa hybrida.*
Common name—Shrub Rose Plant.
Varietal denomination: 'KORcracfir'.

SUMMARY OF THE INVENTION

The new variety of *Rosa hybrida* Shrub Rose Plant of the present invention was created during 2008 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling variety (non-patented in the United States). The male parent (i.e., pollen parent) was the 'NOA75800' variety (non-patented in the United States).

The parentage can be summarized as follows:

unnamed seedling x 'NOA75800'

The seeds resulting from the above pollination were sown and small plants were obtained which were physically and biologically different from each other. Selective study resulted in the identification of a single plant of the new variety.

It was found that the new Shrub Rose Plant of the present invention possesses the following combination of characteristics:

(a) abundantly and substantially continuously forms attractive, salmon-orange colored blossoms,
(b) exhibits a compact and bushy growth habit,
(c) forms vigorous vegetation, (d) forms attractive ornamental semi-glossy, dark green foliage, and
(e) exhibits very good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling female parent (i.e., seed parent) displays a lower petal count and has a different flower color than that of the new variety. Additionally, the 'NOA75800' variety (i.e., pollen parent) exhibits a different flower color and is less vigorous than the new variety. Moreover, the new variety can be readily distinguished from non-parental related similar varieties. For example, the 'HARpageant' variety (U.S. Plant Pat. No. 22,587) exhibits a fragrance, provides orange-apricot colored blossoms and displays more petals compared to the new variety, whereas the new variety exhibits no noticeable fragrance and provides salmon-orange colored blossoms. In addition, the 'Radral' variety (U.S. Plant Pat. No. 19,803) exhibits a strong citrus-rose fragrance and displays more petals compared to the new variety, whereas the new variety exhibits no noticeable fragrance.

The new variety has been found to undergo asexual propagation in Klein Offenseth-Sparrieshoop, Germany by a number of routes such as budding. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORcracfir'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately two years of age and were observed at Jacksonville, Oreg. during September 2015 while growing outdoors on their own roots.

FIG. 1—illustrates a specimen of a plant displaying floral buds and flowers at varying points of opening.

Figure 2:
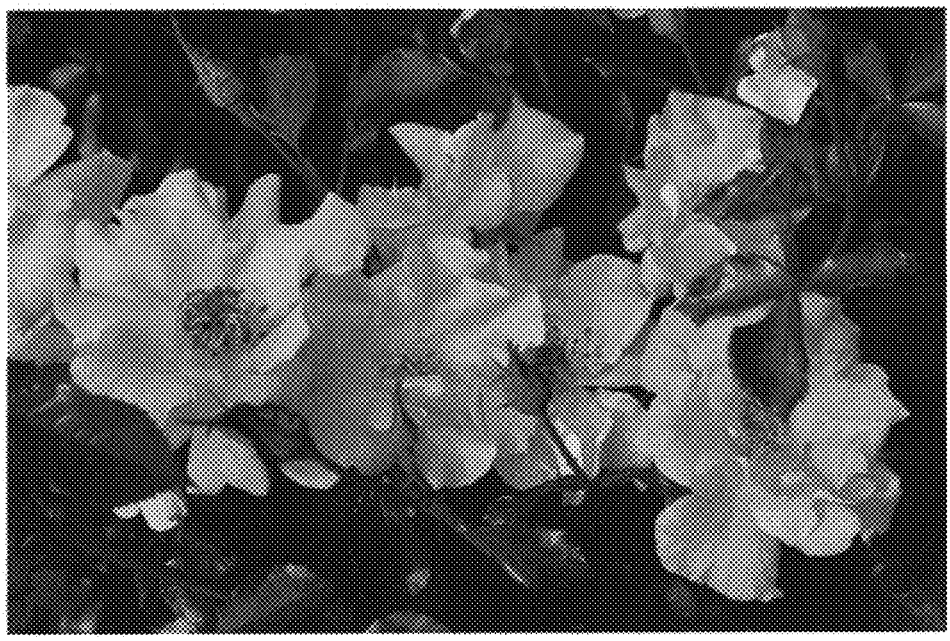

FIG. 2—illustrates specimen of flowers in the course of opening.

Figure 3:
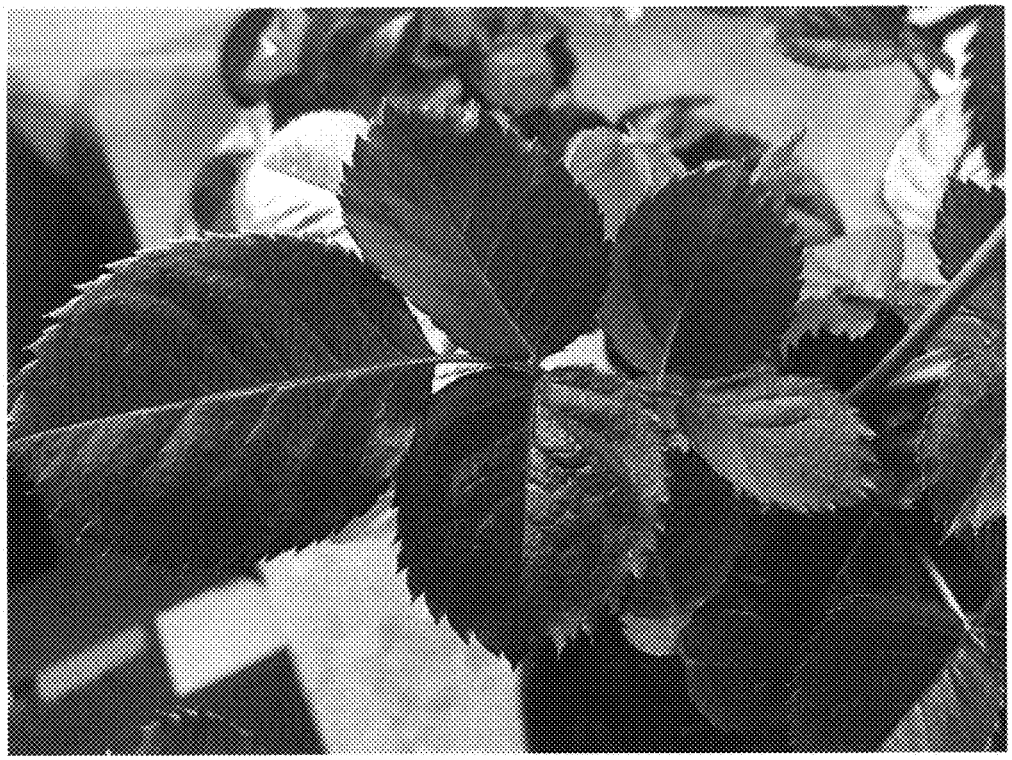

FIG. 3—illustrates specimen of the foliage—plane view—obtuse.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during August, while growing in a one-gallon container on its own roots at Cochranville, Pa.

Class: Shrub Rose Plant.

Plant:

*Habit*.—Compact, very bushy, and upright.

*Height*.—Approximately 45.0 cm on average from the top of the soil plane.

*Width*.—Approximately 45.0 cm on average.

Branches:

*Stem color*.—Old wood is commonly near Green Group 138A transitions to Greyed-Orange Group 177B as it hardens; young stems are commonly near Green Group 143A.

*Main stem length*.—Approximately 40.0 cm on average.

*Secondary stem length*.—Approximately 10.0 to 15.0 cm on average.

*Surface texture*.—Mature stems are a mixture of smooth and rough as the stems begin to turn woody; immature stems are smooth.

*Thorns*.—Amount: commonly 7 thorns per 10.0 cm of stem. Young thorns: length is approximately 6.0 mm on average, width is approximately 3.0 mm at point of attachment on average, and color is commonly near Yellow-Green Group 145A. Old thorns: length is approximately 7.0 mm on average, width is approximately 4.0 mm at point of attachment on average, and color is commonly near Greyed-Orange Group 177A.

Foliage:

*General appearance*. Semi-glossy, dark green.

*Young foliage*.—Upper surface color: commonly a blend of near Green Group NN137 and Greyed-Purple Group 183A. Under surface color: commonly a blend of near Green Group 137C and Greyed-Purple Group 183C.

*Old foliage*.—Upper surface color: commonly near Green Group 137A. Under surface color: commonly near Green Group 137C.

*Petiole*.—Upper surface: texture is glabrous, color is commonly near Green Group 137B. Under surface: texture is glabrous, color is commonly near Green Group 137D. Length: approximately 2.0 cm on average.

*Rachis*.—Color: upper surface is commonly near Green Group 137B, under surface is commonly near Green Group 137D. Size: length is approximately 5.5 cm on average. Surface texture: smooth with a few small prickles on the under surface.

*Stipules*.—Length: approximately 11.0 mm on average. Width: approximately 5.0 mm on average. Margin: entire to erose. Color: upper surface is commonly near Yellow-Green Group 144B; lower surface is commonly near Yellow-Green Group 144C.

*Leaf margin*.—Serrate.

*Leaf arrangement*.—Odd pinnate.

Leaflets:

*Number*.—3, 5, and 7.

*Shape*.—Ovate.

*Venation*.—Pattern is reticulate and color is commonly near Greyed-Purple Group 183C.

*Texture*.—Upper surface is smooth; lower surface is smooth.

*Size*.—Terminal leaflet: length is approximately 6.0 cm on average; width is approximately 3.0 cm on average. Lower leaflets: length is approximately 3.5 cm on average and width is approximately 2.0 cm on average. 5-Leaflet leaf: length is approximately 10.0 cm on average and width is approximately 8.5 cm on average.

*Terminal leaflet general*.—Glossiness intensity of upper surface is strong; margin undulation is weak; apex shape is acute; base shape is rounded.

Inflorescence:

*Number of flowers*.—Approximately 26 blooms open on average on a plant at once.

*Number of blooms per stem or in a cluster*.—Commonly 1 bloom per stem on average.

*Type*.—Solitary inflorescence.

*Size*.—Length is approximately 7.0 cm on average; and width is approximately 7.0 cm on average.

*Peduncle*.—Color: commonly Yellow-Green Group 144A. Diameter: approximately 2.0 mm on average. Length: approximately 5.0 cm on average. Surface texture: glabrous.

*Sepals*.—Number: commonly 5. Upper surface color and texture: covered in short pubescence and color is commonly near Yellow-Green Group 144A. Under surface color and texture: puberulent and color is commonly near Yellow-Green Group 144B. Size: length is approximately 1.5 cm on average and width is approximately 6.0 mm on average. Shape: lanceolate; apex is acute to aristate. Margin: entire with occasional extensions on two or three sepals measuring approximately 3.0 mm in length and approximately 1.0 mm in width.

*Bud*.—Shape: ovoid. Size: length is approximately 2.0 cm on average; width is approximately 1.5 cm on average. Color (when opening): commonly near Yellow-Orange Group 16A blending to Red Group 43B towards the apex.

*Flower*.—Salmon-orange colored. Form: semi-double, cuplike Shape: rounded. Diameter: approximately 7.0 cm on average. Height: approximately 2.5 cm on average. Duration: commonly on the plant approximately 5 days. Color upper surface when opening/after opening/fully open: commonly near Yellow Group 13A at the point of attachment blending to near Orange-Red Group 32C and Orange-Red Group 32B towards the apex; basal spot color is commonly near Yellow Group 13A. Color under surface upon opening/after opening/fully open: commonly mostly near Yellow Group 13B with some blending of Orange-Red Group 31B at the margins.

*Fragrance*.—None noticeable.

*Petal*.—Number: approximately 9 on average. Drop: excellent. Length: approximately 3.0 cm on average. Width: approximately 3.0 cm on average. Shape: overall shape is broadly obovate; apex is round; and base is cuneate. Texture: upper and under surface is glabrous. Margin: entire; margin undulation is strong.

*Petaloids*.—Color upper surface when opening/after opening/fully open: commonly near Yellow Group 13A at the point of attachment blending to near Orange-Red Group 32C and Orange-Red Group 32B towards the apex; basal spot color is commonly near Yellow Group 13A. Color under surface upon opening/after opening/fully open: commonly mostly near Yellow Group 13B with some blending of Orange-Red Group 31B at the margins.

*Stamen*.—Number: approximately 80 on average. Anthers: number is about 80 and color is commonly near Orange Group 26A; length is approximately 4.0 mm on average. Filaments: length is approximately 8.0 mm on average and color is commonly near Yellow-Orange Group 23A.

*Pistils*.—Arrangement: separate and free. Number: approximately 56. Style: color is commonly near Yellow-Green Group 144D with some color of near Greyed-Purple Group 185C just below the stigma; length is approximately 1.0 cm on average. Stigma: color is commonly near Yellow-Green Group 151D; diameter is commonly less than 1.0 mm on average.

*Receptacle*.—Achenes stand on the bottom and wall; diameter is approximately 8.0 mm on average, shape is round, color is commonly near Yellow-Green Group 144A, and surface texture is smooth.

*Pollen*.—None observed.

*Hips*.—None observed.

Development:

*Vegetation*.—Dark green, vigorous, semi-glossy, and strong.

*Hardiness zone*.—USDA Zone 6b.

*Blooming*.—Abundant and substantially continuous from spring through frost.

*Tolerance to diseases*.—Very good.

Plants of the 'KORcracfir' variety have not been observed under all possible environmental conditions to date. Accordingly, it is possible that the phenotypic expression may vary somewhat with changes in light intensity and duration, cultural practices, and other environmental conditions.

I claim:

1. A new and distinct Shrub Rose Plant characterized by the following combination of characteristics:

(a) abundantly and substantially continuously forms attractive, salmon-orange colored blossoms, (b) exhibits a compact and bushy growth habit, (c) forms vigorous vegetation, (d) forms attractive ornamental semi-glossy, dark green foliage, and (e) exhibits very good disease resistance;

substantially as herein shown and described.

* * * * *